US008741358B2

(12) United States Patent
Asaka et al.

(10) Patent No.: US 8,741,358 B2
(45) Date of Patent: *Jun. 3, 2014

(54) GHRELIN PRODUCTION PROMOTER

(75) Inventors: Masahiro Asaka, Sapporo (JP); Hiroshi Takeda, Sapporo (JP); Ryuuji Takasaki, Minato-ku (JP); Tomohisa Hattori, Inashiki-gun (JP)

(73) Assignees: National University Corporation Hokkaido University, Sapporo-shi (JP); Tsumura & Co., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/345,826

(22) Filed: Jan. 9, 2012

(65) Prior Publication Data

US 2012/0107426 A1   May 3, 2012

Related U.S. Application Data

(60) Continuation of application No. 12/876,476, filed on Sep. 7, 2010, now Pat. No. 8,182,845, which is a division of application No. 12/162,864, filed as application No. PCT/JP2006/325155 on Dec. 18, 2006, now abandoned.

(30) Foreign Application Priority Data

Jan. 31, 2006   (JP) ................................. 2006-022794

(51) Int. Cl.
*A61K 36/00*   (2006.01)
*A61K 36/284*   (2006.01)
*A61K 36/25*   (2006.01)
*A61K 36/8888*   (2006.01)
*A61K 36/076*   (2006.01)
*A61K 36/484*   (2006.01)
*A61K 36/725*   (2006.01)
*A61K 36/752*   (2006.01)
*A61K 36/258*   (2006.01)
*A61K 36/48*   (2006.01)
*A61K 36/906*   (2006.01)

(52) U.S. Cl.
USPC ........... 424/725; 424/728; 424/757; 424/756; 424/736

(58) Field of Classification Search
None
See application file for complete search history.

(56) References Cited

FOREIGN PATENT DOCUMENTS

| JP | 6 128165 | 5/1994 |
|----|----------|--------|
| JP | 9 87187 | 3/1997 |
| JP | 2004 520392 | 7/2004 |
| JP | 2005 507949 | 3/2005 |
| JP | 2005 239712 | 9/2005 |
| WO | 03 097083 | 11/2003 |
| WO | 2004 014412 | 2/2004 |

OTHER PUBLICATIONS

Goso et al, Effects of traditional herbal medicine on gastric mucin against ethanol-induced gastric injury in rats, Comparative biochemistry and physiology. Part C, Pharmacology, toxicology & endocrinology, (Jan. 1996) vol. 113, No. 1, pp. 17-21.*

Kanitani et al, A single oral dose toxicity study and a 13-week repeated dose study with a 4-week recovery period of Tsumura Rikkunshi-to (TJ-43) in rats. Japanese Pharmacology and Therapeutics, (1995) vol. 23, No. Suppl. 7, pp. 225-240.*

Tatsuta et al, Effect of treatment with liu-jun-zi-tang (TJ-43) on gastric emptying and gastrointestinal symptoms in dyspeptic patients. Alimentary pharmacology & therapeutics, (Aug. 1993) vol. 7, No. 4, pp. 459-462.*

Varkonyi et al, Gastric emptying, neuropathy status and digestive symptoms in type-1 diabetes mellitus. Is there a relationship? Gastroenterology, (Apr. 2001) vol. 120, No. 5 Supplement 1, pp. A.468.*

Fukuda et al, Ghrelin enhances gastric motility through direct stimulation of intrinsic neural pathways and capsaicin-sensitive afferent neurones in rats. Scandinavian journal of gastroenterology, (Dec. 2004) vol. 39, No. 12, pp. 1209-1214.*

Tack et al, Influence of ghrelin on gastric emptying and meal-related symptoms in gastroparesis. Gastroenterology, (Apr. 2004) vol. 126, No. 4, Suppl. 2, pp. A485.*

Takeda, H. at al., "Improvement of Anorexia by Rikkunshitovia Increased Ghrelin Secreation, Gastroenterology", vol. 130, No. 4, pp. A543-A544, (2006).

Zhang, W. et al., Experimental Study of Liujunzi decoction against Chronic Obstructive Pulmonary Disease, Shandong Medical Journal, vol. 46, No. 32, pp. 14-15, (2006).

Fu, S., "Chusei I Ketsugo Chiryo Ronen Mansei Shikian' en 82 Rei Hokoku", Guangdong Medical Journal, vol. 20, No. 7, abstract, onlineInternet. URL:http://www.wanfangdata.com.cn/gikan/periodical.Articles/gdyx/gdyx99/gdyx9907/990748.htm, 1999.

Yamakuni, T. et al., "Shinkei Eiyo Inshi Kassel o Yusuru Tennen Seiri Kasseibutsu no Tansaku to Alzheimer Byo Chiryoyaku Kaihatsu eno Oyo", Folia Pharmacologica Japonica, vol. 124, pp. 67-68, (2004).

(Continued)

*Primary Examiner* — Qiuwen Mi
(74) *Attorney, Agent, or Firm* — Oblon, Spivak, McClelland, Maier & Neustadt, L.L.P.

(57) ABSTRACT

The objectives are to find a substance or a composition capable of promoting the production of ghrelin with physiological activities such as growth hormone secretion effect, and to provide a pharmaceutical comprising it as the active ingredient. The pharmaceutical is a ghrelin production promoter comprising Rikkunshi-to as the active ingredient.

3 Claims, 1 Drawing Sheet
(1 of 1 Drawing Sheet(s) Filed in Color)

(56) References Cited

OTHER PUBLICATIONS

Oizumi, Y. et al., "Mi Kaimei Seibutsu Gensho o Tsukasadoru Kagi Kagaku Busshitsu Shinkei Saibo no Bunka o Seigyo Suru Biryo Tennen Seiri Kassel Busshitsu no Tansaku Oyobi Sono Sayo Kaiseki, Mikaimei Seibutsu Gensho o Tsukasadoru Kagi Kagaku Busshitsu", pp. 100-103, (2004).

Yoshizato, H. et at., Stimulation of Growth Hormone Gene Expressionin the Pituitary and Brain by Panax ginseng C. A. C.A. Meyer, Endoctrine Journal, vol. 46, pp. S85-S86, (1999).

Murase, K. et al., Nerve Growth Factor-like ImmunoreactiveSubstance in Panax ginseng Extract, Biosci. Biotechnol. Biochem., vol. 58, No. 9, pp. 1638-1641, (1994).

Sakamoto, Y., et al., "Clinical effects of Hochu-e kiki-to and Rikukunshi-to for anorexia in theadministrations of anticancer drugs and interferon, Gendai Igaku," vol. 14, No. 2, pp. 96-99 (1993).

Goso, et al., Effects of traditional herbal medicine on gastric mucin against ethanol-induced gastric injury in rats, Comparative biochemistry and physiology. Part C, Pharmacology, toxicology & endocrinology, (Jan. 1996) vol. 113, No. 1, pp. 17-21.

Journal of the Japanes Society of Gastroenterology, 101:A705 (Sep. 2004) w/English Translation.

\* cited by examiner

* and **: P < 0.05 vs control by Dunnett's analysis. N=8

, ##: P < 0.05 and 0.01 vs normal by student-t-test. * and
**: P < 0.05 vs control by Dunnett's analysis. N=8

: P < 0.05 vs normal by student-t-test. N=7
CIS: Cisapride 5 mg/kg, SB: SB242084 7 mg/kg,
MET: Metoclopropamide 10 mg/kg

GHRELIN PRODUCTION PROMOTER

CROSS-REFERENCE TO RELATED APPLICATIONS

This application is a continuation of U.S. Ser. No. 12/876,476 filed Sep. 7, 2012, now U.S. Pat No. 8,182,845, which is a divisional of U.S. Ser. No. 12/162,864 filed Jul. 31, 2008, abandoned, which was a National Stage of PCT/JP06/325155 filed Dec. 18, 2006 and claims the benefit of JP 2006/022784 filed Jan. 31, 2006.

TECHNICAL FIELD

The present invention relates to a novel pharmaceutical such as ghrelin production promoter comprising "Rikkunshi-to" (a kind of kampo medicine) as the active ingredient.

BACKGROUND ART

Ghrelin is a peptide hormone discovered in 1999 that is known to promote the secretion of growth hormone (GH). Ghrelin promotes GH secretion via receptors different from those for growth hormone-releasing hormone (GHRH). The peptide chain of ghrelin comprises 28 amino acid residues, in which the hydroxyl group of the third serine is acylated with octanoic acid (active ghrelin); but non-acylated ghrelin (desacyl ghrelin) does not exhibit GH secretion activity.

Various physiological active mechanisms of ghrelin are known; and for example, ghrelin is known to increase appetite, protect the cardiovascular system, and control metabolism among other effects, in addition to the above-mentioned GH secretion-promoting effect. These known effects of ghrelin suggest that the possibility of its application to therapeutic agents for diseases such as cibophobia, myocardial infarction, heart failure, and cachexia as well as those to prevent aging/dwarfism (Non-Patent Document 1). Moreover, it is reported that ghrelin promotes neurite extension and improves nerve paralysis (including movement disorders and perceptual disorders) associated with peripheral nerve diseases such as amyotrophic lateral sclerosis, diabetic neurological disorder, neuropathy, neurological disorder caused by traumatic neural damage or neural deficiency, toxic neurological disorder and multiple sclerosis. It also improves memory disorders in patients with central nerve disorders and diseases such as Alzheimer's disease, vascular dementia, Parkinson's disease, Huntington's disease and spinal injury; it is useful in the treatment of dementia and for brain function activation; as well as to treat and prevent amyotrophic lateral sclerosis and diabetic neurological disorder (Patent Document 1). It is also known for its activation of osteoblasts and bone reconstitution in dwarfism and normal persons; increase of muscle mass and muscle strength in GH-deficient adults; improvement of exercise capacity in GH-deficient adults; and cure of severe burns in children. It is used in combination with gonadotropin to induce ovulation; in the prevention of protein metabolism disorder due to prednisone administration; in the promotion of T-cell education in severe immunodeficiency; and prevention of senile weight loss, fatty tissue extension and skin atrophy. As for the effects of ghrelin in patients with disorders not directly related to GH deficiency or depression, ghrelin may, for example, increase heart beating and is therefore known to be effective in cardiac diseases such as heart failure (Patent Document 2). Also known are its effects on myocardial infarction, reperfusion injury in bypass surgery or PTCA for myocardial infarction, coronary microcirculation failure, myocarditis (alcoholic, viral, etc.), dilated cardiomyopathy, cardiac transplantation, arrhythmia, heart failure, and also drug-induced myocardial disorders caused by chemotherapeutical agents or the like (Patent Document 3). In addition, it has been confirmed that ghrelin administration to patients with chronic obstructive pulmonary disease (COPD) results in an increase of respiration muscle power, body weight and skeletal muscle mass, as well as in an improvement of the QOL score and the 6-minute walking distance; it is also reported that ghrelin may be expected to improve various symptoms of COPD (Non-Patent Document 2).

As in the above, various excellent physiological effects of ghrelin have been specifically noted, and the development of pharmaceuticals comprising ghrelin as the active ingredient has been promoted. However, few substances have heretofore been known capable of promoting ghrelin production in living bodies.

Patent Document 1: JP-A 2005-239712
Patent Document 2: Re-issued WO03097083
Patent Document 3: Re-issued WO04014412
Non-Patent Document 1: Proceedings the 124th Symposium of the Japanese Association of Medical Science, pp. 45-52
Non-Patent Document 2: New Current 16 (27), pp. 17-22

DISCLOSURE OF THE INVENTION

Problems to be Solved by the Invention

The present invention has been made in consideration of the technical background described above, and its objectives are to find a substance or composition that will promote ghrelin production in living bodies and to provide a pharmaceutical comprising it as the active ingredient.

Means for Solving the Problems

The present inventors have assiduously investigated substances and compositions that may promote ghrelin production. In the end, they found that "Rikkunshi-to", a kind of kampo medicine has an excellent ghrelin production-promoting effect, and have completed the present invention.

Specifically, the invention is a ghrelin production promoter comprising Rikkunshi-to as the active ingredient.

Effect of the Invention

According to the invention, it is possible to provide a pharmaceutical, which may effectively increase the production of acylated active ghrelin and be an effective treatment for patients with disorders associated with growth hormone deficiency or depression such as dwarfism, central nerve disorders such as Alzheimer's disease, and cardiac disorders such as myocardial infarction.

The pharmaceutical of the invention has an excellent safety profile with few problems such as side effects, since the active ingredient Rikkunshi-to has been used traditionally as a prescription drug in Japan and China.

BEST MODE FOR CARRYING OUT THE INVENTION

Rikkunshi-to used as the active ingredient in the invention is a type of kampo medicine that contains crude drugs such as ATRACTYLODIS LANCEAE RHIZOMA, GINSENG RADIX, PINELLIAE TUBER, POLIA, ZIZYPHI FRUCTUS and others described in the classics of kampo medicine formulation (Manbyo Kaishun); it promotes gastric emptying and increase gastric mucosal blood flow, and is used as a therapeutic agent for gastritis and gastric atony.

The compounding range (composition) of the crude drugs in the Rikkunshi-to is generally as follows:

ATRACTYLODIS LANCEAE RHIZOMA (JP *Atractylodes Lancea* Rhizome) or ATRACTYLODIS RHIZOMA (JP *Atractylodes* Rhizome) 3.0 to 4.0
GINSENG RADIX (JP Ginseng) 2.0 to 4.0
PINELLIAE TUBER (JP Pinellia Tuber) 3.0 to 4.0
POLIA (JP *Poria Sclerotium*) 3.0 to 4.0
ZIZYPHI FRUCTUS (JP Jujube) 2.0
AURANTII NOBILIS PERICARPIUM (JP Citrus Unshiu Peel) 2.0 to 4.0
GLYCYRRHIZAE RADIX (JP *Glycyrrhiza*) 1.0 to 1.5
ZINGIBERIS RHIZOMA (JP Ginger) 0.5 to 2.0

Of the compounding range, the especially preferred Rikkunshi-to is obtained from a mixture of the crude drugs of ATRACTYLODIS LANCEAE RHIZOMA 4.0, GINSENG RADIX 4.0, PINELLIAE TUBER 4.0, POLIA 4.0, ZIZYPHI FRUCTUS 2.0, AURANTII NOBILIS PERICARPIUM 2.0, GLYCYRRHIZAE RADIX 1.0 and ZINGIBERIS RHIZOMA 0.5.

In the ghrelin production promoter of the invention, either Rikkunshi-to having the above-mentioned composition itself or its extract can be used as the active ingredient of a pharmaceutical formulation prepared using known carriers for pharmaceuticals.

The extract of Rikkunsi-to can be prepared according to classical methods in which a mixture of the crude drugs mixed at the compounding ratio mentioned above is extracted with 5 to 20 volumes of an appropriate aqueous solvent followed by solid-liquid separation. Examples of the preferred aqueous solvent are water, ethanol and aqueous solution of acetic acid. The extraction method can be hot or cold extraction. In particular, extraction conducted at 90 to 100° C. using water as the solvent is preferred.

The obtained extract of Rikkunshi-to may be dried into powder if necessary. Although the extract, in liquid or powder state, can be directly administered as it is, it may also be formulated into an extract preparation for easy administration and convenient carrying. For example, a mixture of the crude drugs is extracted with 10 volumes of hot water followed by solid-liquid separation. The obtained liquid extract is concentrated and dried, and the resulting dried powder extract of Rikkunshi-to is formulated as diluted powder, granules, tablets or capsules according to conventional methods by mixing it with appropriate fillers (such as lactose, corn starch and crystalline cellulose), excipients or the like, which are commonly used for pharmaceutical formulations.

The ghrelin production promoter of the invention may be administered as any formulation for oral use, or for parenteral use such as injection or infusion.

Formulations for oral use include solid ones such as powder, granules, tablets and capsules, and liquid ones such as suspensions, emulsions, syrups, and elixirs; and pharmaceutical carriers may be used in accordance with the administration routes and formulations.

As for solid formulations for oral use, the usable carriers are starch, lactose, sugar, mannitol, carboxymethyl cellulose, corn starch, inorganic salts, etc. Furthermore, optional components such as binders, disintegrating agents, surfactants, lubricants, fluidity accelerators, corrigents, coloring agents and perfumes may be compounded as needed.

Of the above optional components, examples of the binders include starch, dextrin, acacia, gelatin, hydroxypropyl starch, methyl cellulose, sodium carboxymethyl cellulose, hydroxypropyl cellulose, crystalline cellulose, ethyl cellulose, polyvinyl pyrrolidone, and macrogol.

Examples of the disintegrating agents include starch, hydroxypropyl starch, sodium carboxymethyl cellulose, calcium carboxymethyl cellulose, carboxymethyl cellulose and low-substituted hydroxypropyl cellulose.

Examples of the surfactants include sodium laurylsulfate, soybean lecithin, sucrose fatty acid ester and Polysorbate 80. Examples of the lubricants include talc, waxes, hydrogenated vegetable oil, sucrose fatty acid ester, magnesium stearate, calcium stearate, aluminium stearate, polyethylene glycol. Examples of the fluidity accelerators include light silicic anhydride, dried aluminium hydroxide gel, synthetic aluminium silicate and magnesium silicate.

As for formulations for parenteral use, these may be produced as follows: The active ingredient, Rikkunshi-to or its extract is dissolved or suspended in distilled water for injection, physiological saline water, aqueous sucrose water, vegetable oil for injection, sesame oil, peanut oil, soybean oil, corn oil, propylene glycol, polyethylene glycol or the like according to conventional methods; if desired, a microbicide, a preservative, a stabilizer, a tonicity agent, an analgesic or the like, may be added thereto.

The dose of the ghrelin production promoter of the invention described above may vary depending on the administrating route, the disease condition and others; but in general, for oral administration, the dose may be from 500 to 1000 mg/kg/day or so of Rikkunshi-to extract.

As already described, ghrelin is effective for activation of osteoblasts and bone reconstitution inpatients with dwarfism and in normal persons, increases muscle mass and muscle strength in GH-deficient adults, and improves in exercise capacity of GH-deficient adults, etc. Therefore, the ghrelin production promoter comprising Rikkunshi-to as the active ingredient may be used as a growth hormone secretion promoter.

Ghrelin is known to contribute to treatment of myocardial infarction, reperfusion injury after bypass surgery or PTCA for myocardial infarction, coronary microcirculation failure, myocarditis (alcoholic, viral, etc.), dilated cardiomyopathy, cardiac transplantation, arrhythmia, heart failure, and also myocardial disorders induced by drugs such as chemotherapeutical agents or the like. Consequently, the ghrelin production promoter comprising Rikkunshi-to as the active ingredient may be used as a therapeutic agent in patients with myocardial infarction or heart failure.

Moreover, it is reported that ghrelin promotes neurite extension and improves nerve paralysis (including movement disorders and perceptual disorders) associated with peripheral nerve diseases such as amyotrophic lateral sclerosis, diabetic neurological disorder, neuropathy, neurological disorder caused by traumatic neural damage or neural deficiency, toxic neurological disorder and multiple sclerosis. It also improves memory disorders in patients with central nerve disorders and diseases such as Alzheimer's disease, vascular dementia, Parkinson's disease, Huntington's disease and spinal injury; it is useful in the treatment of dementia and for brain function activation; as well as to treat and prevent amyotrophic lateral sclerosis; the ghrelin production promoter comprising Rikkunshi-to as the active ingredient may be used as a therapeutic agent for patients with Alzheimer's disease.

Besides, it is reported that ghrelin administration to patients with chronic obstructive pulmonary disease (COPD) results in an increase of respiration muscle power, body weight and skeletal muscle mass, as well as in an improvement of the QOL score and the 6-minute walking distance;

and therefore, the ghrelin production promoter comprising Rikkunshi-to as the active ingredient may be used as a therapeutic agent for patients with chronic obstructive pulmonary disease.

EXAMPLES

The invention is described in more detail with reference to the following Examples, however, the invention is not restricted at all by these Examples.

Test Example 1

Ghrelin Production Promotion Test 1:

The ghrelin production promoting effect was investigated in fasted normal rats without anticancer agent treatment. Seven-week-old SD male rats (8/group) were orally administered a test substance Rikkunshi-to (TJ-43, by Tsumura & Co.) at a dose of 100 or 500 mg/kg, and kept fasted for 24 hours. Then, Rikkunshi-to was orally administered again at the same dose and two hours later the rats were decapitated and the blood was collected to determine the concentration of ghrelin by ELISA. Blood was centrifuged at 10,000 rpm for three minutes, then 1 mol HCl was added to the collected supernatant in proportion of $\frac{1}{100}$ of the blood to prepare the test sample. The ghrelin concentration was quantitatively determined using an Active Ghrelin ELISA Kit (by Mitsubishi Kagaku Iatron, Inc.). Rats in the comparative groups were orally administered mosapride (MOS) or metoclopropamide (MET), which are ordinary nausea/vomiting inhibitors. Each dose of MOS was 10 mg/kg, and that of MET was 3 mg/kg. Twenty-five hours after the first administration, dosing of MOS and MET was repeated. The results are shown in FIG. 1. The rats in the control group were administered distilled water in place of the test substance.

The results show that Rikkunshi-to promoted the production of active ghrelin in fasted normal rats.

Test Example 2

Ghrelin Production Promotion Test 2:

The ghrelin production promoting effect was investigated in fasted rats under anticancer agent treatment. Seven-week-old SD male rats (8/group) were orally administered a test substance Rikkunshi-to (TJ-43, by Tsumura & Co.) at a dose of 500 or 1000 mg/kg, and kept fasted for 24 hours. Then, the anticancer agent cisplatin (CDDP) was intraperitoneally administered at a dose of 2 mg/kg. Nearly at the same time, Rikkunshi-to at the same previous dose was orally administered to the rats (2nd administration). Rats of the comparative groups were administered ondansetron (ODS), which is an ordinary nausea/vomiting inhibitor, by subcutaneous injection to the back of each rat, at a dose of 0.4 mg/kg/dose; and 1.5 hours after the CDDP administration, the second dose was administered. Besides, cisapride (CIS), SB242084 (SB) or MET were used as comparative drugs. These were orally administered at a dose of 5 mg/kg (CIS), 7 mg/kg (SB) or 10 mg/kg (MET), respectively, one hour after the CDDP administration. In all the experiments, the rats were decapitated two hours after the CDDP administration and blood was collected to determine the concentration of ghrelin by ELISA. The concentration of active ghrelin was determined for each group, in the same method as in Test Example 1. The results obtained with Rikkunshi-to and ODS are shown in FIG. 2; and those obtained with CIS, SB and MET are shown in FIG. 3. Rats in the normal control group were administered physiological saline instead of CDDP, and distilled water instead of the test substance; those in the control group were administered CDDP, and distilled water instead of the test substance.

In these results, active ghrelin significantly increased in both Rikkunshi-to (500 and 1000 mg/kg) groups. On the other hand, no significant difference was detected in the comparative groups.

Example 1

Production of Rikkunshi-to Extract:

Cut crude drugs—4 kg ATRACTYLODIS LANCEAE RHIZOMA, 4 kg GINSENG RADIX, 4 kg PINELLIAE TUBER, 4 kg POLIA, 2 kg ZIZYPHI FRUCTUS, 2 kg AURANTII NOBILIS PERICARPIUM, 1 kg GLYCYRRHIZAE RADIX and 0.5 kg ZINGIBERIS RHIZOMA—were taken, blended, and added to about 12 volumes of pure water. Then, the mixture was heated up to 95 or 100° C. under stirring. Thereafter, this was extracted for 60 minutes and the extract was processed for solid-liquid separation; then, the separated liquid was concentrated under reduced pressure. The concentrate was mixed with sucrose fatty acid ester added to a final concentration of 1.0% of the solid content of the extract, and dried by spraying to obtain a dried powder extract of Rikkunshi-to, 4.04 kg.

Example 2

Production of Granules:

Lactose (3.4225 kg) and magnesium stearate (0.0375 kg) were added to and mixed with the dried powder extract of Rikkunshi-to (4.04 kg) obtained in Example 1. The mixture was tabletted using a tabletting machine according to conventional methods, and then pulverized, granulated and sieved to obtain good granules.

Industrial Applicability

The ghrelin production promoter of the invention can increase an acylated active ghrelin that has an activity of growth hormone secretion effect and the like.

Accordingly, this is useful as a therapeutic agent for ghrelin-related dwarfism; cardiac diseases such as heart failure and myocardial infarction; and central nerve disorders such as Alzheimer's disease and Parkinson's disease. In addition, the ghrelin production promoter of the invention has an excellent safety profile, since the active ingredient is Rikkunshi-to which has been traditionally used as a prescription drug in Japan and China.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Figure 1:
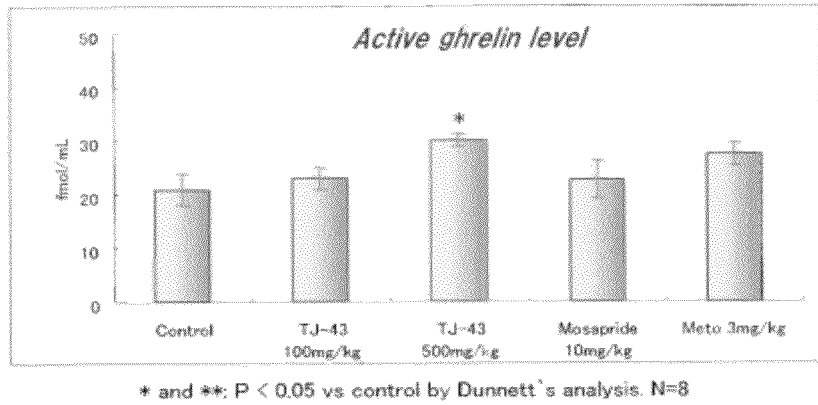
FIG. 1 Concentration of active ghrelin after administration of each test substance in Test Example 1.
Figure 2:
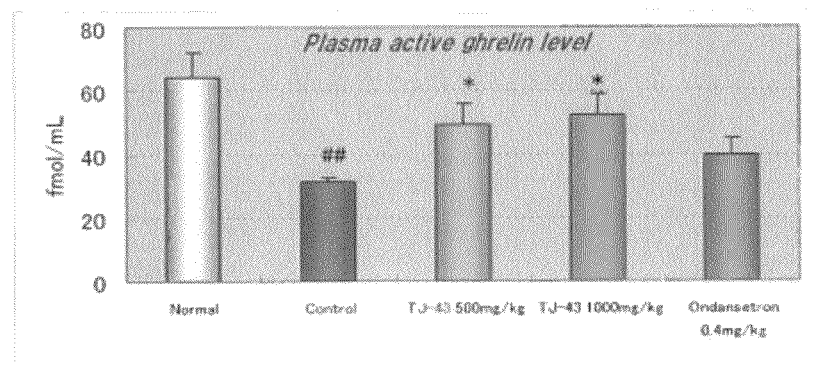
FIG. 2 Concentration of active ghrelin in the Rikkunshi-to and ODS administration groups in Test Example 2.
Figure 3:
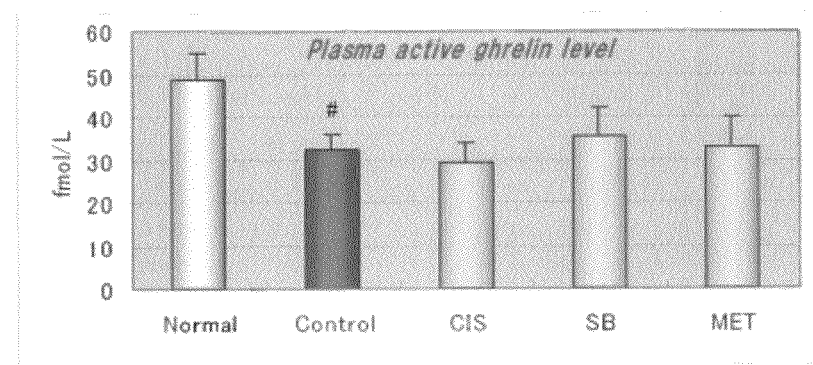
FIG. 3 Concentration of active ghrelin concentration in the CIS, SB and MET administration groups in Test Example 2.

The invention claimed is:

1. A method of promoting production of ghrelin in a human subject in need thereof, the method comprising administering an effective amount of Rikkunshi-to to the human subject, wherein said Rikkunshi-to comprises 3.0 to 4.0 weight parts of *Atractylodes Lancea* or *Atractylodes,* 2.0 to 4.0 weight parts of Ginseng Radix, 3.0 to 4.0 weight parts of Pinelliae Tuber, 3.0 to 4.0 weight parts of *Poria Sclerotium*, 2.0 weight part of *Zizyphi Fructus*, 2.0 to 4.0 weight parts of *Aurantii Nobilis Pericarpium*, 1.0 to 1.5 weight parts of *Glycyrrhiza* Radix, and 0.5 to 2.0 weight parts of Zingiberis Rhizoma, wherein the human subject in need thereof is suffering from reperfusion injury after bypass surgery, reperfusion injury after percutaneous transluminal coronary angioplasty for myocardial infarction, coronary microcirculation failure, myocarditis, dilated cardiomyopathy, cardiac transplantation, arrhythmia, amyotrophic lateral sclerosis, diabetic neurological disorder, neurological disorder caused by traumatic neural damage, neurological disorder caused by neural deficiency, toxic neurological disorder, multiple sclerosis, vascular dementia, Parkinson's disease, Huntington's disease, or spinal injury.

2. The method of claim 1, wherein the human subject in need thereof is suffering from reperfusion injury after bypass surgery, reperfusion injury after percutaneous transluminal coronary angioplasty for myocardial infarction, coronary microcirculation failure, myocarditis, dilated cardiomyopathy, cardiac transplantation, or arrhythmia.

3. The method of claim 1, wherein the human subject in need thereof is suffering from amyotrophic lateral sclerosis, diabetic neurological disorder, neurological disorder caused by traumatic neural damage, neurological disorder caused by neural deficiency, toxic neurological disorder, multiple sclerosis, vascular dementia, Parkinson's disease, Huntington's disease, or spinal injury.

* * * * *